United States Patent [19]

Prochaska

[11] Patent Number: 4,823,457
[45] Date of Patent: Apr. 25, 1989

[54] DISPOSABLE SURGICAL SCALPEL

[75] Inventor: Frank H. Prochaska, Waynesboro, Va.

[73] Assignee: American Safety Razor Company, Verona, Va.

[21] Appl. No.: 184,051

[22] Filed: Apr. 20, 1988

[51] Int. Cl.[4] .............................................. B21D 39/00
[52] U.S. Cl. ........................................ 29/509; 30/340; 30/342; 128/305
[58] Field of Search ................... 29/509; 30/294, 329, 30/333, 337, 339, 342, 343, 344, 335, 340; 128/305, 314, 315

[56] References Cited

U.S. PATENT DOCUMENTS

| | | | |
|---|---|---|---|
| 3,187,431 | 6/1965 | Mattes | 30/339 |
| 3,412,467 | 11/1968 | Matwijcow | 30/335 |
| 3,877,147 | 4/1975 | Cummings | 30/329 |
| 4,034,473 | 7/1977 | May | 128/305 |
| 4,473,076 | 9/1984 | Williams et al. | 128/305 |
| 4,617,738 | 10/1986 | Kopacz | 128/305 |

Primary Examiner—P. W. Echols
Assistant Examiner—K. Jordan
Attorney, Agent, or Firm—Nixon & Vanderhye

[57] ABSTRACT

A method of cold staking a scalpel blade to a scalpel handle wherein the blade has a key slot complementarily configured to a projecting boss formed on the end of the blade handle. The boss has two elements at its opposite ends which project beyond an intermediate portion. When cold staked, the material of the projecting portions flows over the outside surface of the blade to secure the blade to the handle at those points where loading of the blades is anticipated to be a maximum whereas the intermediate portion of the blade receives the boss, which boss is not cold staked at that area to the blade. The handle is formed of a polypropylene having a filler of 25–35% by weight of talc.

19 Claims, 2 Drawing Sheets

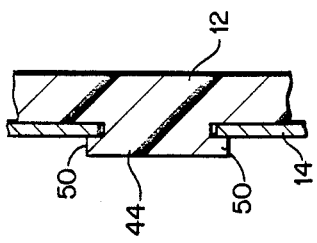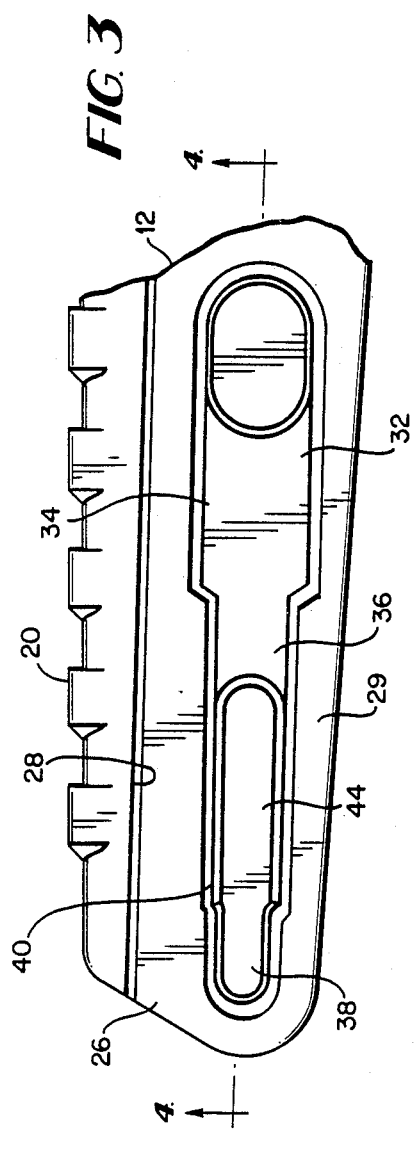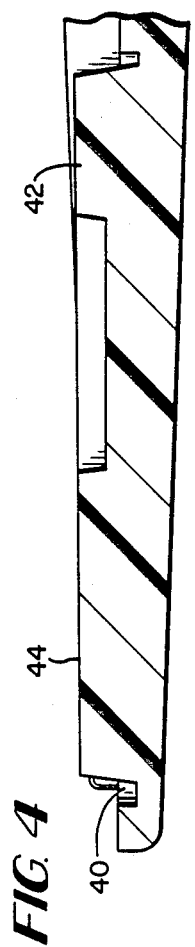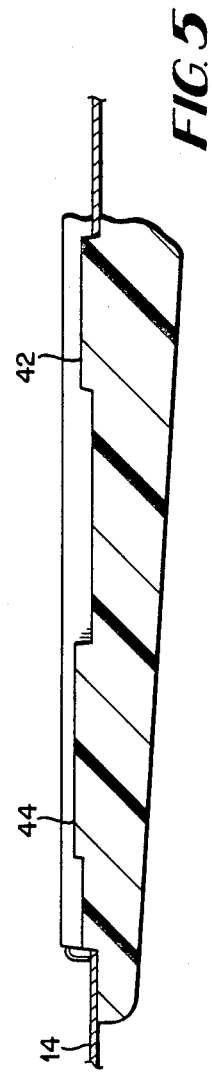

DISPOSABLE SURGICAL SCALPEL

BACKGROUND OF THE INVENTION

The present invention relates to an improved method of securing a surgical scalpel blade and a handle one to the other and particularly relates to a method for cold staking the blade to the handle.

Disposable surgical scalpels typically consist of a stainless steel or carbon steel blade and a separately manufactured molded plastic handle. Consequently, a means for attaching the blade and handle one to the other is required. Conventionally, the handle is molded to provide at one end a seat for interlocking engagement with the outer profile of the tang of the blade. It is also provided with a key which is received in a keyway formed on the blade. Fundamentally, the attachment must be secure enough to transmit anticipated cutting forced from the blade to the handle and sufficiently tight to prevent relative movement between the blade and the instrument.

In conventional disposable surgical scalpels, the key on the handle is made to fit the entire opening in the blade tang. The key extends beyond the outer surface of the blade and is deformed to displace material over the edges of the blade tang keyhole by application of a tool which reduces the height of the key. Two methods of staking are currently used to accomplish this deformation. One method is hot staking which involves use of a heated tool applied to the top of the handle key. The heat transferred from the tool to the plastic softens it and pressure is used to cause the softened plastic to flow out over the blade surface surrounding the keyway, thereby capturing the blade. Problems associated with this method include process control, non-uniformity of final appearance and strength of the overall assembly.

Ultrasonic staking uses a tool similar to that used in hot staking. Rather than being heated, the tool is caused to vibrate at high frequency, i.e., 20,000-40,000 cycles per second. Upon contact with the handle key, the ultrasonic vibration excites the plastic molecules, causing the plastic to soften and flow. The degree of success with respect to ultrasonic staking is a function, however, of the different plastic materials used. Most materials of choice for the manufacture of scalpel handles are only marginal candidates for ultrasonic staking and numerous compromises have to be made to use this method of manufacture.

Recognizing the deficiencies of these prior art techniques, a novel and improved attachment between the scalpel blade and the scalpel handle has been formulated in accordance with the present invention. Starting first with the specification of the material of the handle, criterion of cost, autoclavibility solvent resistance, stiffness and dimensional stability indicate that a filled polypropylene would be optimum. While other manufacturers of disposable scalpels have used polypropylene filled with about 20% talc, it has been found that handles with that material are dimensionally less stable and more flexible than desired. A talc filler of 40% by weight, however, has been found to be too brittle. As part of the present invention, a talc filling for the polypropylene handle material of about 25-35% by weight ultimately produces a handle which can advantageously be cold staked and does not have the disadvantages noted above.

It is also necessary to provide a simple economical strong attachment which lends itself to automatic assembly and produces an aesthetically pleasing appearance. Cold staking is employed in the present invention to accomplish those goals. However, tests conducted with cold staking of full profile handle keys tended to split the blade during manufacture. That is, the plastic material flow completely filled the blade keyhole and, as the stake was completed, split the blade. It was found, after further testing, that the strength of the attachment between the scalpel handle and scalpel blade depended on the ends of the resulting stake rather than in the mid-portion of the stake. The result, therefore, is the adoption of a configuration for a handle key which enabled cold staking of high strength and aeasthetic appearance without splitting the blade. It has also been found that, with such new handle key configuration and concomitant cold staking thereof, superior blade retention and strength under adverse loading conditions are achieved. More particularly, the configuration of the handle key which produces these results provides a mid-portion height of the handle key substantially no greater than the thickness of the blade while the end portions of the handle key have a substantially greater thickness than the thickness of the blade. In this manner, during cold staking in accordance with the present invention, two separate cold staked heads are formed over the blade keyhole. That is, the heads at the opposite ends of the key are staked, whereas the intermediate portion of the key between the end stakes are left unstaked. Forces that would otherwise split the blade are eliminated and the portions of the handle key which carry the greatest load are staked.

In accordance with a particular embodiment of the present invention, there is provided a novel and improved method of securing a surgical scalpel blade and a handle one to the other comprising the steps of providing a surgical scalpel blade with a through keyway and forming a handle having a surface for receiving a side face of the blade adjacent an end of the scalpel handle and a key projecting from the surface. The key has a pair of spaced elements projecting from the surface distances greater than the thickness of the blade and at least one additional element between the spaced elements projecting from the surface a distance substantially no greater than the thickness of the blade. The blade is disposed on the handle with the key received in the keyway and the side face of the blade bearing against the handle surface. The spaced elements are cold staked to overlie portions of the opposite side face of the blade, thereby to secure the blade and handle one to the other. Preferably, the method hereof includes cold staking only the two elements, leaving in final securement the one element between the two elements unstaked. Additionally, the method hereof includes forming the handle of a polypropylene material with a filler, preferably talc, of about 25-35% by weight of the handle material.

Accordingly, it is a primary object of the present invention to provide a novel and improved method for securing a surgical scalpel blade and handle one to the other wherein cold staking is employed in a particular manner to produce a joint of high strength and aesthetically pleasing appearance without blade splitting during manufacture.

These and further objects and advantages of the present invention will become more apparent upon reference to the following specification, appended claims and drawings.

BRIEF DESCRIPTION OF THE DRAWING FIGURES

FIG. 3 is an enlarged fragmentary side elevational view of the scalpel handle and which mounts the blade illustrating the specific construction of the key;

FIG. 4 is a cross-sectional view thereof taken generally about on line 4—4 in FIG. 3;

FIG. 5 is is a cross-sectional view thereof taken generally about on line 5—5 in FIG. 2; and FIG. 6 is a cross-sectional view thereof taken generally about on line 6—6 in FIG. 2.

DETAILED DESCRIPTION OF THE DRAWING FIGURES

Reference will now be made in detail to the present preferred embodiment of the invention, an example of which is illustrated in the accompanying drawings.

Figure 1:
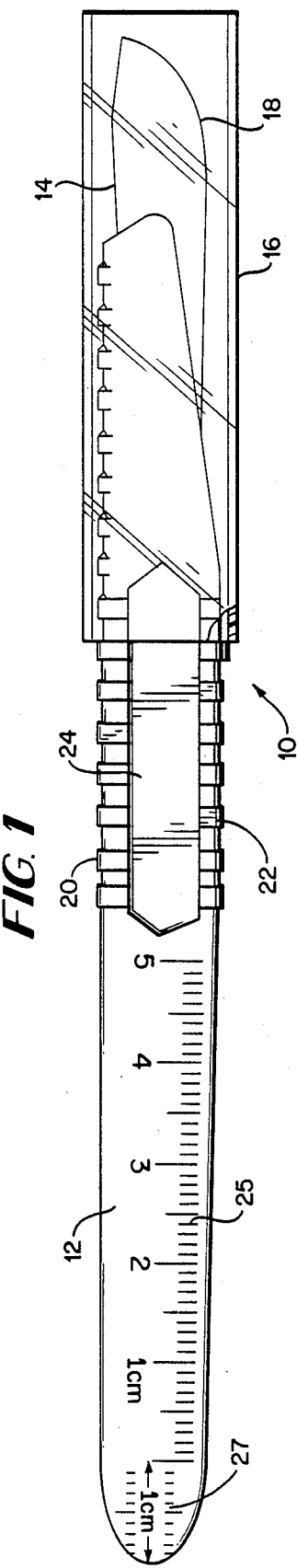
FIG. 1 is a side elevational view of a surgical scalpel constructed in accordance with the present invention with a scalpel blade guard illustrated applied to the scalpel.
Figure 2:
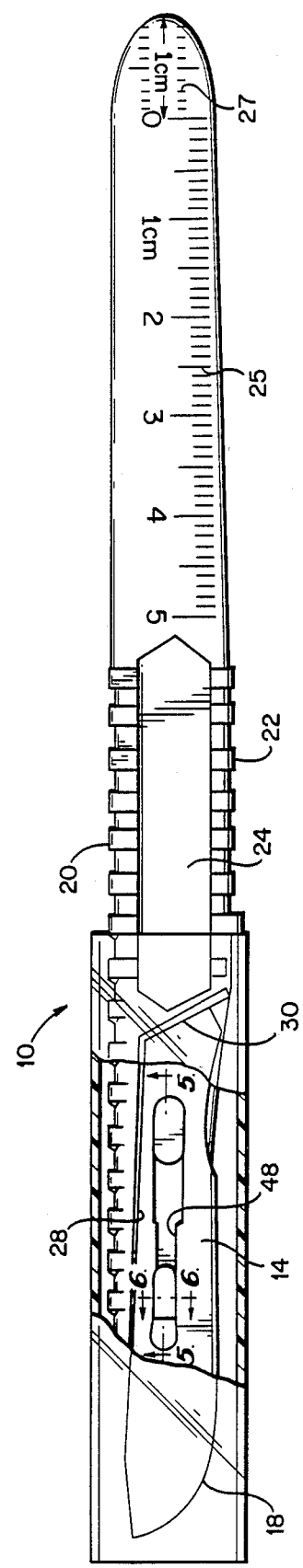
FIG. 2 is a view similar to FIG. 1, illustrating the opposite side of the scalpel and guard with portions of the guard broken out and in cross-section to illustrate details of the securement of the scalpel blade to the scalpel handle.

Referring now to the drawing figures, particularly to FIGS. 1 and 2, there is illustrated a surgical scalpel constructed in accordance with the present invention and generally designated 10. The scalpel 10 comprises an elongated handle 12 and a scalpel blade 14 mounted adjacent an end of the scalpel handle. As illustrated in FIGS. 1 and 2, the scalpel blade and end of the handle on which the blade is mounted is encapsulated or encased within a guard 16, which forms no part of the present invention. Guard 16 comprises a sleeve which receives the scalpel blade and handle end such that the blade edge 18 lies within a protective casing.

Handle 12 is preferably formed of a plastic material such as polypropylene and has a filler of talc. As discussed previously, the talc filler should comprise between about 25-35% by weight of the polypropylene material inasmuch as it has been determined that a scalpel having a talc filler greater than that range has been found too brittle and less than that range provides a dimensionally less stable handle and one which is also more flexible than desired.

On the top side of the handle there is provided a plurality of ridges 20 spaced longitudinally one from the other for purposes of providing a surface against which the surgeon's finger may bear in non-slip relation. The lower edge of the scalpel handle also is provided with a plurality of ribs 22 spaced longitudinally one from the other for like purposes. One of the ribs 22 is enlarged along the underside and serves as a stop for the guard 16 so that the guard may be telescopically positioned on the blade handle end in overlying relation to the blade without being further axially displaced along the handle. The sides of the scalpel handle 12 are centrally recessed at 24 to provide an area wherein the logo of the manufacturer may be placed. Also, scales 25 and 27 may be provided along the end of the handle opposite the blade end. Preferably, one scale 25 extends longitudinally along the underside of the blade handle on both sides thereof, with gradations longitudinally spaced one from the other. Another scale 27 extends centrally along the long axis of the handle but adjacent the tip remote from the blade.

Referring now particularly to FIG. 3, the end of the scalpel handle 12 on which the blade 14 is mounted is provided with an elongated recess 26 along one side thereof. That is, one side of the handle adjacent the blade end is inset from the remaining portions of that side such that the blade, when disposed in the recess or inset, lies along the longitudinal place bisecting the handle. The recess 26 is defined in part by an upper margin 28 with a rear angled inclined wall 30 (FIG. 2). Disposed along the face 29 of the recess 26 is a shaped key. The key includes a boss which projects laterally from the face 29 toward the open side of the recess 26. Key 32 is elongated and comprises stepped portions 34, 36 and 38, respectively, of decreasing width from right to left as seen in FIG. 3. The portions 34, 36 and 38 are outlined in the face 29 of the recess by a groove 40. The base portion 34 includes a laterally projecting first element or boss 42 which projects laterally beyond the face of the remaining portions of base portion 34. The intermediate and distal portions 36 and 38 have a laterally projecting second element or boss 44, which projects beyond the face of the remaining part of the intermediate portion 36 and for the entirety of end portion 38. Consequently, portions of base portion 34 and intermediate portion 36 adjoining one another and which forms a third element lie at a reduced lateral projection in comparison with the elements 42 and 44. Elements 42 and 44 also have side walls which taper inwardly toward one another in a direction away from the face 30 of recess 26.

Blade 14 has a key slot 48 (FIG. 2) which is complementarily shaped to the key 32. Thus, upon application of the blade 14 to the handle end, the key slot 48 receives the key 32 and the majority of the inside surface of the blade butts the recessed surface 26. The tapered walls of the elements 42 and 44 facilitate insertion of the key into the key slot. It will be appreciated that once the blade is received by the key, the elements 42 and 44 project beyond the face of the blade 14 opposite recess surface 26, whereas the reduced laterally projecting portions of the base and intermediate portions 34 and 36 extend into the key slot and lie substantially flush with the side of the blade face remote from recess surface 26.

In accordance with the present invention, the blade may now be cold staked to the scalpel handle by means of a staking tool, not shown. Upon application of the staking tool, the plastic material forming the elements 42 and 44 flows laterally to form flanges 50 which overlie the margins of the key slot formed in the blade. In this manner, the staking is provided in the areas of the blade and handle wherein the flo of material does not completely fill the blade keyhole and, as a consequence, does not have a tendency to split the blade upon cold staking. Moreover, cold staking at the opposite ends of the key and key slot provides mounting strength in those areas of the attachment in which the maximum forces tending to separate the blade from the handle are applied. That is, forces which split the blades are confined to the ends of the blade key slot where the blade is better able to withstand the loading.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of securing a surgical scalpel blade and a handle one to the other, comprising the steps of:
   providing a surgical scalpel blade with a through keyway;
   forming the handle with a blade receiving surface adjacent an end thereof for receiving a side face of the blade and a key projecting from said surface, said key having spaced first and second elements projecting from said surface distances greater than the thickness of the blade and a third element between said first and second elements projecting from said surface a distance substantially no greater than the thickness of said blade;
   disposing said blade on said handle with said key received in said keyway and a side face of the blade bearing against the blade receiving surface; and
   cold staking said first and second elements to overlie portions of the opposite side face of the blade to secure the blade and handle one to the other.

2. A method according to claim 1 including cold staking only said first and second elements, leaving, in final securement, said third element unstaked.

3. A method according to claim 1 including forming said handle of a polypropylene material having a filler of about 20–40% by weight of the handle material.

4. A method according to claim 3 including providing a filler of talc.

5. A method according to claim 4 wherein the filler is about 25–35% by weight of the handle material.

6. A method according to claim 1 including forming the key with first and second elongated portions of different widths, and forming in said blade a complementary shaped keyway having a pair of elongated portions of different widths, said first element being located along said first key portion and said second element being located along said second key portion.

7. A method according to claim 6 including forming said second element adjacent an end of said second elongated portion and remote from said first elongated portion.

8. A method according to claim 7 including forming said first and second elements at opposite ends of said first and second portions, respectively.

9. A method according to claim 1 including the step of forming the edges of said key to taper outwardly from said surface in a convergent direction.

10. A method according to claim 1 including the step of forming the key and keyway substantially complementary in shape whereby, when said blade is disposed on said handle, the key and keyway cooperate to preclude movement of the blade relative to the handle in the plane of the blade.

11. A method of securing a surgical scalpel blade and a handle one to the other, comprising the steps of:
    providing a surgical scalpel blade with a through opening;
    forming the handle with a blade receiving surface adjacent an end thereof for receiving a side face of the blade and a key projecting from said surface, said key having spaced first and second elements projecting from said surface distances greater than the thickness of the blade;
    disposing said blade on said handle with said key received in said blade opening and the side face of the blade bearing against the handle surface; and
    cold staking said first and second elements to overlie portions of the opposite side face of the blade at spaced positions therealong to secure the blade and handle one to the other.

12. A method according to claim 11 including forming said key with a third element between said first and second element projecting from said surface a distance substantially no greater than the thickness of the blade and cold staking only said first and second elements leaving in final securement said third element unstaked.

13. A method according to claim 11 including forming said handle of a polypropylene material having a filler of about 20–40% by weight of the handle material.

14. A method according to claim 13 including providing a filler of talc.

15. A method according to claim 14 wherein the filler is about 25–35% by weight of the handle material.

16. A method according to claim 11 including forming an elongated key with first and second portions of different extent in the direction of a plane containing said surface, and forming a complementary shaped blade opening having complementary portions of different extent, said first element being located along said first portion and said second element being located along said second portion.

17. A method according to claim 16 including forming said spaced first and second elements at opposite ends of said elongated key.

18. A method according to claim 11 including the step of forming the edges of said key to taper outwardly from said surface in a convergent direction.

19. A method according to claim 11 including the step of forming the key and blade opening substantially complementary in shape whereby, when said blade is disposed on said handle, the key and opening cooperate to preclude movement of the blade relative to the handle in the plane of the blade.

* * * * *